United States Patent [19]

Hamashima et al.

[11] 4,183,928
[45] Jan. 15, 1980

[54] HALOARYLMALONAMIDOOXACEPH-ALOSPORINS

[75] Inventors: Yoshio Hamashima, Kyoto; Masayuki Narisada, Ibaraki; Sadao Hayashi, Ashiya; Wataru Nagata, Nishinomiya, all of Japan

[73] Assignee: Shionogi And Co., LTD., Osaka, Japan

[21] Appl. No.: 900,235

[22] Filed: Apr. 26, 1978

[30] Foreign Application Priority Data

Apr. 28, 1977 [JP] Japan .................................. 52-49630
Aug. 25, 1977 [JP] Japan .................................. 52-102260

[51] Int. Cl.² ................. C07D 413/02; A61K 31/395; A61K 31/535
[52] U.S. Cl. .................................. 424/248.52; 544/90
[58] Field of Search ................. 544/21, 90; 424/248.52

[56] References Cited

U.S. PATENT DOCUMENTS

| | | | |
|---|---|---|---|
| 4,013,653 | 3/1977 | Wolfe | 544/90 |
| 4,045,438 | 8/1977 | Haviv et al. | 544/21 |
| 4,048,311 | 9/1977 | Berges | 544/21 X |

OTHER PUBLICATIONS

Lednicer et al., The Organic Chemistry of Drug Synthesis, pp. 416–421, John Wiley and Sons, 1977.
Firestone et al., J. Med. Chem., vol. 20, pp. 551–556, Apr. 1977.

*Primary Examiner*—John D. Randolph
*Attorney, Agent, or Firm*—Wenderoth, Lind & Ponack

[57] ABSTRACT

Antibacterial haloarylmalonamido-1-dethia-1-oxacephalosporins of the following formula:

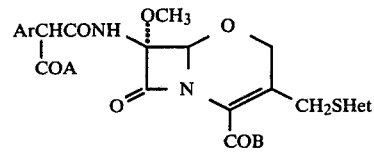

wherein
Ar is

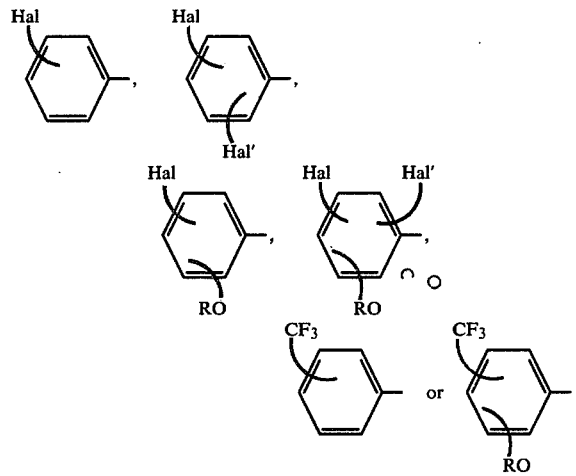

(in which Hal and Hal' each is halogen and
RO is hydroxy or protected hydroxy);
COA and COB each is carboxy or protected carboxy including a pharmaceutically acceptable salt group;
and Het is 1-lower alkyl-5-tetrazolyl, 1,3,4-thiadiazol-2-yl or 5-lower alkyl-1,3,4-thiadiazol-2-yl, a pharmaceutical or veterinary composition comprising the said haloarylmalonamido-1-dethia-1-oxacephalosporin and pharmaceutical carrier, and a method for treating or preventing human or veterinary infectious diseases comprising administering an effective amount of the said antibacterial compound.

8 Claims, No Drawings

HALOARYLMALONAMIDOOXACEPHALOSPORINS

This invention relates to haloarylmalonamido-1-dethia-1-oxacephalosporins. More specifically, it relates to novel 7β-(halogenated arylmalonamido)-7α-methoxy-3-(optionally alkylated tetrazol-5-yl or 1,3,4-thiadiazol-2-yl)thiomethyl-1-dethia-1-oxa-3-cephem-4-carboxylic acids or their derivatives at the carboxy groups. The objective compounds are represented by the following formula:

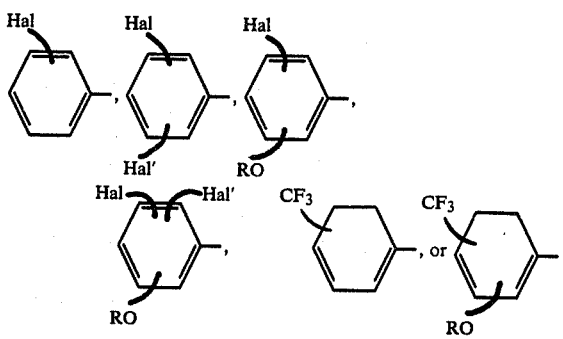

wherein
Ar is

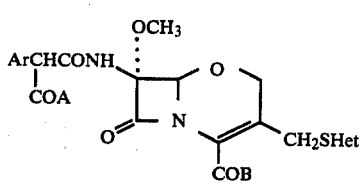

(in which Hal and Hal' each is halogen and RO is hydroxy or protected hydroxy);

COA and COB each is carboxy or protected carboxy including pharmaceutically acceptable salt group; and Het is 1-lower alkyl-5-tetrazolyl, 1,3,4-thiadiazol-2-yl, or 2-lower alkyl-1,3,4-thiadiazol-5-yl.

(1) BACKGROUND OF THE INVENTION

Cephalosporin analogues having oxygen in place of sulfur atom in the nucleus have been described in the Journal of Heterocyclic Chemistry, Volume 5, page 779 (1968) by J. C. Sheehan and M. Dadic; German Patent Application (OLS) No. 2,219,601 (1972); the Canadian Journal of Chemistry, Volume 52, page 3996 (1974) by S. Wolfe et al.; the Journal of the American Chemical Society, Volume 96, page 7582 (1974) by B. G. Christensen et al.; Japanese Patent unexamined Publication No. 49-133,594; Japanese Patent unexamined Publication No. 51-149,295 by Beecham Group Ltd.; and Japanese Patent Unexamined Publication No. 52-65,292.

In a previous invention made by two of the present inventors, it was found that the compounds of the following formula had superior characters to the known and described compounds:

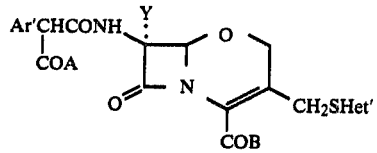

(Compounds of the previous invention)

(wherein
Ar' is phenyl, thienyl, hydroxyphenyl, or acyloxyphenyl;
COA and COB each is carboxy or protected carboxy;
Het' is 1-methyltetrazolyl when Y is methoxy, or is 1-methyltetrazolyl, 2-methyl-1,3,4-thiadiazol-5-yl or 1-carboxymethyltetrazolyl when Y is hydrogen; and
Y is hydrogen or methoxy).

Now, according to this invention, one or more halogens are introduced into the aryl part (Ar') attached to the malonamido groups to achieve some improvements in antibacterial activities and pharmacodynamic properties. These improvements form the bases for this invention.

(2) COMPOUNDS OF THE INVENTION

The compounds of this invention are represented by the formula I given above and include novel 7β-(halogenated arylmalonamido)-7α-methoxy-3-(optionally lower alkyl-substituted tetrazol-5-yl or 1,3,4-thiadiazol-2-yl)thiomethyl-1-dethia-1-oxa-3-cephem-4-carboxylic acids and their derivatives at the carboxy groups (I).

In the formula I, said halogen shown by Hal or Hal' each is the same or different representing fluorine, chlorine, bromine or iodine.

The protected hydroxy represented by OR includes those to avoid undesirable side-reactions at the hydroxy during due reactions or to improve the biological activities. They include known protecting groups which can be readily removed without adverse effects on other parts of the molecule. Representatives of the protected hydroxy include acyloxy for example, $C_1$ to $C_9$ carboxylic acyloxy (e.g. formyloxy, acetyloxy, phenylacetoxy, benzoyloxy, thienylacetoxy or cinnamoyloxy), $C_1$ to $C_6$ carbamoyloxy (e.g. carbamoyloxy, methylcarbamoyloxy, ureidocarbonyloxy, or 1-piperidinylcarbonyloxy), $C_2$ to $C_{11}$ alkoxycarbonyloxy optionally substituted by halogen (e.g. methoxycarbonyloxy, ethoxycarbonyloxy, cyclopropylmethoxycarbonyloxy, t-butoxycarbonyloxy, trichloroethoxycarbonyloxy, iodoethoxycarbonyloxy or isobornyloxycarbonyloxy), monocyclic or dicyclic aralkoxycarbonyloxy optionally substituted by halogen, $C_1$ to $C_3$ alkoxy, $C_1$ to $C_3$ alkyl, $C_1$ to $C_3$ alkylsulfonyl, methylenedioxy, amino, nitro, cyano or the like (e.g. benzyloxycarbonyloxy, tolylmethoxycarbonyloxy, xylylmethoxycarbonyloxy, anisyloxycarbonyloxy, aminobenzyloxycarbonyloxy, nitrobenzyloxycarbonyloxy or diphenylmethoxycarbonyloxy); monocyclic or dicyclic aralkoxy optionally substituted by halogen, $C_1$ to $C_3$ alkyl, $C_1$ to $C_3$ alkoxy, $C_1$ to $C_3$ alkylsulfonyl, methylenedioxy, amino, nitro, cyano, or the like (e.g. benzyloxy, tolyloxy, xylylmethoxy, anisyloxy, dimethoxybenzyloxy, methylenedioxybenzyloxy, nitrobenzyloxy, aminobenzyloxy, diphenylmethoxy, dimethoxydiphenylmethoxy or naphthylmethoxy); silyloxy (e.g. trimethylsilyloxy, dimethoxymethylsilyloxy, methoxydimethylsilyloxy, methylenedioxymethylsilyloxy or chlorodimethylsilyloxy); stannyloxy (e.g. trimethylstannyloxy); and the similar protected hydroxy. The phenolic hydroxy can form a salt with a strong base (e.g. sodium, potassium or quaternary ammonium salt).

COA and COB each is the same or different representing a carboxy or carboxylic acid salt group. Alternatively, COA and COB each is a protected carboxy for stabilizing the compounds during synthesis or for oral administration to humans. The protection can be in a form of ester, amide, acid halide, acid anhydride, hydrazide, salts, or the like, which can be deprotected without adverse effects on other parts of the molecule. For example, COA or COB can be those forming $C_1$ to $C_{10}$ alkyl esters (e.g. methyl, ethyl, propyl, isopropyl, butyl, t-butyl, monohydroxy-t-butyl, methoxy-t-butyl, cyclopropylmethyl, cyclopropylethyl, pentyl, isopentyl, cyclopentyl, octyl or isobornyl ester), $C_1$ to $C_6$ haloalkyl esters (e.g. chloromethyl, chloroethyl, bromoethyl, iodoethyl, dichloropropyl, trichloroethyl, trichlorobutyl or dibromocyclohexyl ester), $C_3$ to $C_{10}$ acylalkyl esters (e.g. acetylethyl, propionylmethyl, phenacyl, chlorophenacyl, bromophenacyl, nitrophenacyl or dicarboxymethyl ester), $C_3$ to $C_{10}$ alkoxyalkyl esters (e.g. methoxymethyl, ethoxymethyl, chloroethoxymethyl, propoxyethyl, butoxyethyl, cyclohexyloxyethyl, methoxyethoxymethyl, butoxyethoxymethyl or octyloxyethyl ester), $C_2$ to $C_{10}$ aminoalkyl esters (e.g. aminomethyl, aminoethyl, dimethylaminoethyl or pyrrolidinomethyl esters), monocyclic or dicyclic aryl esters optionally having halogen, nitro, amino, $C_1$ to $C_3$ alkyl, $C_1$ to $C_3$ alkoxy, $C_1$ to $C_3$ alkylsulfonyl or cyano as a substituent (e.g. phenyl, chlorophenyl, nitrophenyl, naphthyl, pyridyl, indolyl, indanyl or pentachlorophenyl), monocyclic, dicyclic or tricyclic aralkyl esters optionally having $C_1$ to $C_3$ alkyl, $C_1$ to $C_3$ alkoxy, $C_1$ to $C_3$ alkylsulfonyl, cyano or halogen as a substituent (e.g. benzyl, methylbenzyl, xylylmethyl, chlorobenzyl, bromobenzyl, anisyl, ethoxybenzyl, nitrobenzyl, dibromobenzyl, phenethyl, phthalidyl, p-hydroxydi-t-butylbenzyl, diphenylmethyl, trityl or anthrylmethoxy ester), $C_1$ to $C_{10}$ alkylsilyl esters (e.g. trimethylsilyl, dimethylmethoxysilyl, chlorodimethylsilyl or ethylenedioxymethylsilyl ester), $C_1$ to $C_{10}$ alkylstannyl esters (e.g. trimethylstannyl ester), mixed anhydrides with $C_1$ to $C_{10}$ organic or inorganic acid (e.g. mixed anhydride with acetic, propionic, methoxyformic, ethoxyformic, butoxyformic, methanesulfonic, ethanesulfonic, benzenesulfonic, sulfuric or perchloric acid), $C_1$ to $C_{10}$ hydrocarbyl thioesters (e.g. thiol methyl ester), $C_1$ to $C_5$ alkylamides (e.g. methylamide, ethylamide, butylamide or pentylamide), di-$C_1$ to $C_5$ alkylamide (e.g. dimethylamide, diethylamide, piperidinylamide, morpholinoamide or methylmorpholinoamide), hydrazides (e.g. 1,2-diisopropylhydrazide or 1,2-dibutylhydrazide), alkali metal salts (e.g. lithium, sodium or potassium salt), alkaline earth metal salts (e.g. magnesium, calcium or acetoxycalcium salt), $C_1$ to $C_{15}$ hydrocarbylammonium salts (e.g. triethylammonium, N-methylmorpholinium, dimethylanilinium or dicyclohexylammonium salt), and similar protected carboxy. In the objective Compounds I, the protected carboxy can be a pharmaceutically and/or pharmacologically acceptable salt or ester group. Other protecting groups are to be replaced by those groups during the course of synthesis. Therefore, the structure of the latter protecting groups can be widely varied without departing from the gist of this invention.

Suitable lower alkyl in Het is $C_1$ to $C_3$ alkyl and can be methyl, ethyl, propyl or isopropyl.

Preferable Ar is monohydroxymonohalophenyl (e.g. 2-hydroxy-3-fluorophenyl, 2-hydroxy-4-fluorophenyl, 2-hydroxy-5-fluorophenyl, 2-hydroxy-6-fluorophenyl, 3-hydroxy-2-fluorophenyl, 3-hydroxy-4-fluorophenyl, 3-hydroxy-5-fluorophenyl, 3-hydroxy-6-fluorophenyl, 4-hydroxy-2-fluorophenyl, 4-hydroxy-3-fluorophenyl, 2-hydroxy-3-chlorophenyl, 2-hydroxy-4-chlorophenyl, 2-hydroxy-5-chlorophenyl, 2-hydroxy-6-chlorophenyl, 3-hydroxy-2-chlorophenyl, 3-hydroxy-4-chlorophenyl, 3-hydroxy-5-chlorophenyl, 3-hydroxy-6-chlorophenyl, 4-hydroxy-2-chlorophenyl, 4-hydroxy-3-chlorophenyl, 4-hydroxy-2-bromophenyl or 4-hydroxy-3-bromophenyl) or the corresponding monocarbamoyloxymonohalophenyl, or in the case of intermediates, the said monohydroxymonohalophenyl can be protected at its hydroxy by a conventional protecting group (e.g. t-butoxycarbonyl, benzyloxycarbonyl, trichloroethoxycarbonyl, cyclopropylmethoxycarbonyl, cyclopropylethoxycarbonyl, benzyl, methylbenzyl, dimethylbenzyl, isobutylbenzyl, anisyl, nitrobenzyl, trimethylsilyl, t-butyldimethylsilyl or methoxydimethylsilyl). Especially valuable are 4-hydroxy-2-fluorophenyl and 3-hydroxy-6-fluorophenyl.

Preferable COA and COB groups include carboxy or its pharmaceutically acceptable salt (e.g. sodium, potassium, magnesium, or calcium salt), its pharmaceutically acceptable ester (e.g. phthalidyl, acetoxymethyl, pivaloyloxymethyl, acetoxyethyl, propionyloxyethyl, indanyl, phenyl, tolyl, dimethylphenyl, methoxyphenyl, methoxycarbonyloxyethyl, ethoxycarbonylethyl, phenacyl, or the like ester), or its easily deprotectable ester (e.g. benzyl, anisyl, nitrobenzyl, diphenylmethyl, t-butyl or trichloroethyl ester).

Preferable lower alkyl in Het is methyl.

Antibacterially preferable Het is 1-methyltetrazol-5-yl.

Representative examples of Compound I include the following haloarylmalonamidooxacephalosporins.

7β-(α-o-fluorophenyl-α-carboxyacetamido)-7α-methoxy-3-(1-methyltetrazol-5-yl)thiomethyl-1-dethia-1-oxa-3-cephem-4-carboxylic acid, 7β-(α-o-fluorophenyl-α-carboxyacetamido)-7α-methoxy-3-(1,3,4-thiadiazol-2-yl)thiomethyl-1-oxa-1-dethia-3-cephem-4-carboxylic acid, 7β-(α-o-fluorophenyl-α-carboxyacetamido)-7α-methoxy-3-(2-methyl-1,3,4-thiadiazol-5-yl)thiomethyl-1-dethia-1-oxa-3-cephem-4-carboxylic acid, 7β-(α-o-chlorophenyl-α-carboxyacetamido)-7α-methoxy-3-(1-methyltetrazol-5-yl)thiomethyl-1-dethia-1-oxa-3-cephem-4-carboxylic acid, 7β-(α-o-chlorophenyl-α-carboxyacetamido)-7α-methoxy-3-(1,3,4-thiadiazol-2-yl)thiomethyl-1-dethia-1-oxa-3-cephem-4-carboxylic acid, 7β-(α-o-chlorophenyl-α-carboxyacetamido)-7α-methoxy-3-(2-methyl-1,3,4-thiadiazol-5-yl)-thiomethyl-1-dethia-1-oxa-3-cephem-4-carboxylic acid, 7β-(α-m-fluorophenyl-α-carboxyacetamido)-7α-methoxy-3-(1-methyltetrazol-5-yl)thiomethyl-1-dethia-1-oxa-3-cephem-4-carboxylic acid, 7β-(α-m-fluorophenyl-α-carboxyacetamido)-7α-methoxy-3-(1,3,4-thiadiazol-2-yl)thiomethyl-1-dethia-1-oxa-3-cephem-4-carboxylic acid, 7β-(α-m-fluorophenyl-α-carboxyacetamido)-7α-methoxy-3-(2-methyl-1,3,4-thiadiazol-5-yl)thiomethyl-1-dethia-1-oxa-3-cephem-4-carboxylic acid, 7β-(α-m-chlorophenyl-α-carboxyacetamido)-7α-methoxy-3-(1-methyltetrazol-5-yl)thiomethyl-1-dethia-1-oxa-3-cephem-4-carboxylic acid, 7β-(α-m-chlorophenyl-α-carboxyacetamido)-7α-methoxy-3-(1,3,4-thiadiazol-2-yl)thiomethyl-1-dethia-1-oxa-3-cephem-4-carboxylic acid, 7β-(α-m-chlorophenyl-α-carboxyacetamido)-7α-methoxy-3-(2-methyl-1,3,4-thiadiazol-5-yl)thiomethyl-1-dethia-1-oxa-3-cephem-4-carboxylic acid, 7β-(α-p-fluorophenyl-α-carboxyacetamido)-7α-methoxy-3-(1-methyltetrazol-5-yl)thiomethyl-1-dethia-1-oxa-3-cephem-4-carboxylic acid, 7β-(α-p-fluorophenyl-α-carboxyacetamido)-7α-methoxy-3-(1,3,4-thiadiazol-2-yl)thiomethyl-1-dethia-1-oxa-3-cephem-4-carboxylic acid, 7β-(α-p-fluorophenyl-α-carboxyacetamido)-7α-methoxy-3-(2-methyl-1,3,4-thiadiazol-5-yl)thiomethyl-1-dethia-1-oxa-3-cephem-4-carboxylic acid, 7β-(α-p-chlorophenyl-α-carboxyacetamido)-7α-methoxy-3-(1-methyltetrazol-5-yl)thiomethyl-1-dethia-1-oxa-3-cephem-4-carboxylic acid, 7β-(α-p-chlorophenyl-α-carboxyacetamido)-7α-methoxy-3-(1,3,4-thiadiazol-2-yl)thiomethyl-1-dethia-1-oxa-3-cephem-4-carboxylic acid, 7β-(α-p-chlorophenyl-α-carboxyacetamido)-7α-methoxy-3-(2-methyl-1,3,4-thiadiazol-5-yl)thiomethyl-1-dethia-1-oxa-3-cephem-4-carboxylic acid, 7β-[α-(3-fluoro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(3-fluoro-4-hydroxyphenyl)-α-carboxyacetamido]-7α-methoxy-3-(1,3,4-thiadiazol-2-yl)thiomethyl-1-dethia-1-oxa-3-cephem-4-carboxylic acid, 7β-[α-(2-chloro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(2-chloro-4-hydroxyphenyl)-α-carboxyacetamido]-7α-methoxy-3-(2-methyl-1,3,4-thiadiazol-5-yl)thiomethyl-1-dethia-1-oxa-3-cephem-4-carboxylic acid, 7β-[α-(3-chloro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(3-chloro-4-hydroxyphenyl)-α-carboxyacetamido]-7α-methoxy-3-(1,3,4-thiadiazol-2-yl)thiomethyl-1-dethia-1-oxa-3-cephem-4-carboxylic acid, 7β-[α-(2-trifluoromethyl-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(4-fluoro-2-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(4-fluoro-2-hydroxyphenyl)-α-carboxyacetamido]-7α-methoxy-3-(2-methyl-1,3,4-thiadiazol-5-yl)thiomethyl-1-oxa-1-dethia-3-cephem-4-carboxylic acid, 7β-[α-(4-chloro-2-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(2,3-difluoro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(2,5-difluoro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(2-fluoro-5-chloro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(5-fluoro-2-chloro-4-hydroxyphenyl)-α-carboxyacetamido]-7α-methoxy-3-(2-methyl-1,3,4-thiadiazol-5-yl)thiomethyl-1-dethia-1-oxa-3-cephem-4-carboxylic acid, 7β-[α-(2,3-dichloro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(2,5-dichloro-4-hydroxyphenyl)-α-carboxyacetamido]-7α-methoxy-3-(1-methyltetrazol-5-yl)thiomethyl-1-dethia-1-oxa-3-cephem-4-carboxylic acid, and a pharmaceutically acceptable salt or ester thereof. The said salt or ester implies mono- and di-salts esters and mixtures thereof.

More preferable group of Compounds I includes the following hydroxyhaloarylmalonamido derivatives:

7β-[α-(2-fluoro-4-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(2-fluoro-5-hydroxyphenyl)-α-carboxyacetamido]-7α-methoxy-3-(1-methyltetrazol-5-yl)thiomethyl-1-dethia-1-oxa-3-cephem-4-carboxylic acid, 7β-[α-(2-fluoro-4-hydroxyphenyl)-α-carboxyacetamido]-7α-methoxy-3-(1,3,4-thiadiazol-2-yl)thiomethyl-1-dethia-1-oxa-3-cephem-4-carboxylic acid, 7β-[α-(2-fluoro-5-hydroxyphenyl)-α-carboxyacetamido]-7α-methoxy-3-(1,3,4-thiadiazol-2-yl)thiomethyl-1-dethia-1-oxa-3-cephem-4-carboxylic acid, 7β-[α-(2-fluoro-4-hydroxyphenyl)-α-carboxyacetamido]-7α-methoxy-3-(2-methyl-1,3,4-thiadiazol-5-yl)thiomethyl-1-dethia-1-oxa-3-cephem-4-carboxylic acid, 7β-[α-(2-fluoro-5-hydroxyphenyl)-α-carboxyacetamido]-7α-methoxy-3-(2-methyl-1,3,4-thiadiazol-5-yl)thiomethyl-1-dethia-1-oxa-3-cephem-4-carboxylic acid, and a pharmaceutically acceptable salt (e.g. sodium, potassium or calcium salt) or ester (e.g. 5-indanyl, phenyl, tolyl, lower alkanoyloxymethyl, lower alkyloxycarbonyloxyethyl or phenacyl ester) thereof. The said salt or ester implies mono- or di-salts and esters and mixtures thereof.

(Use)

As stated above, Compounds I are novel substances showing potent antibacterial activities against gram positive and negative bacteria and are useful as medicines, veterinary drugs, and disinfectants. For example, they are conventionally administered orally or parenterally to humans or animals in a daily dose of e.g. 0.05 to 50 mg/kg body weight.

They can be used for treating or preventing infections caused by gram positive bacteria (e.g. *Staphylococcus aureus, Streptococcus pyogenes, Bacillus subtilis, Bacillus cereus, Diplococcus pneumoniae, Corynebacterium diphtheriae*) or gram negative bacteria (e.g. *Escherichia coli,*

*Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi,* or *Serratia marsescens*). The compounds can also be used as disinfectants for preventing decay of perishables, as additives to feedstuffs or as preventor of bacterial beings in hygienical materials.

Further, Compounds I are also useful intermediates for preparing useful β-lactam antibiotics within or beyond the scope of Compounds I.

The Compounds I can be used in a wide variety of oral or parenteral dosage forms solely or in admixture with other coacting substances. The pharmaceutical compositions may be a mixture of 0.01% to 99% of Compound I with a pharmaceutical carrier which can be a solid material or liquid material in which the compounds are mixed, dissolved, dispersed, or suspended. The composition can be in a unit dosage form. The composition can take the solid form of a tablet, powder, dry syrup, troche, granule, capsule, pill, suppository or like solid preparation. Further, the composition can take a liquid form e.g. injection, ointment, dispersion, inhalant, suspension, solution, emulsion, syrup, or elixir. The composition may be flavored or colored. The tablets, granules and capsules may be coated.

All diluents (e.g. starch, sucrose, lactose, calcium carbonate, kaoline); bulking agents (e.g. lactose, fructose, xylitol, sugar, salt, glycine, starch, calcium carbonate, calcium phosphate, kaoline, bentonite, talc or sorbitol); binders (e.g. starch, acacia, gelatin, glucose, sodium alginate, tragacanth, carboxymethyllcellulose, syrup, sorbitol or polyvinylpyrrolidone); disintegrators (e.g. starch, agar, carbonates or sodium laurylsulfate); lubricants (e.g. stearic acid, talc, paraffin, boric acid, silica, sodium benzoate, polyethylene glycol, cacao oil or magnesium stearate), emulsifying agents (e.g. lecithin, sorbitan monooleate or acacia); suspensing agents (e.g. sorbitol, methyl cellulose, glucose, or sugar syrup, gelatin, hydroxyethylcellulose, carboxymethylcellulose, aluminum stearate gel or hydrogenated fats); solvents (e.g. water, buffer solution, peanut oil, sesame oil or methyl oleate), preservatives (e.g. methyl or ethyl p-hydroxybenzoate or sorbic acid); edible coloring agents, aromatic substances, solubilizing agents, buffers, stabilizing agents, analgesics dispersing agents, wetting agents, antioxidants and the like can be available according to conventional methods in the art, if such agents do not exert adverse effect on the compounds.

As in members of β-lactam antibiotics, Compounds I are not so stable to storage for a long time, when mixed with various substances. Substantially pure compounds and a few inert additives are more preferable to make a drug in practice (e.g. vials or capsules).

Compounds I having one or two carboxylic acid salt groups are readily soluble in water and can be used for intravenus, intramuscular or subcutaneous injection as in their aqueous solutions. The pharmaceutical solutions in aqueous solvent may be kept in an ampoule, but generally it is more preferable for prolonged storage to make a vial preparation containing crystals, powder, microcrystals or lyophilizate of Compound I which is dissolved or suspended in the said solvents for injection before use. The preparation may contain preferably said preservative. The vial preparation or injection can be administered to a patient at a daily dose of e.g. 0.05 to 50 mg/kg body weight, such a dosage depending on the condition of the patient, type of infecting bacteria and interval administration.

Compounds I in which COA is a pharmaceutically acceptable ester grouping (e.g. indanyl, acetoxymethyl, pivaloyloxymethyl, ethoxycarbonyloxyethyl, phenacyl, phthalidyl, phenyl, tolyl, xylyl, methoxyphenyl or methoxymethyl) can be easily absorbed through digestive tracts and can be administered orally to human or veterinary subjects.

Further, Compounds I can be used as suppositories, ointments for topical or ocular use, powders for topical use and like preparations available by methods well-known to those skilled in the art. The preparation can contain 0.01 to 99% of the Compound I together with a necessary amount of pharmaceutical carrier given above. A dosage of e.g. 1 μg to 1 mg of the said preparation can be applied to the infected part to be cured.

This invention also provides a method for treating or preventing human or veterinary bacterial infections by administering to human or animal subjects an effective amount of Compound I (at a daily dose of e.g. 0.05 to 50 mg/kg of body weight for injection, e.g. 0.5 to 200 mg/kg body weight for oral administration or e.g. 1 μg to 1 mg for topical application), in an interval of e.g. 3 to 12 hours.

The method is applicable for treating or preventing infectious diseases caused by bacteria sensitive to Compound I (e.g. pneumonia, bronchitis, pneumonitis, empyema, nasopharyngitis, tonsillitis, rhinitis, dermatitis, pustulosis, ulceration, abses, wound or soft tissue infection, ear infection, osteomyelitis, septicemis, gastroenteritis, enteritis, urinary tract infection or pyelonephritis), when caused by such bacteria sensitive to Compound I.

Preferably, Compound I is given to a patient in the form of a pharmaceutical preparation, e.g. powder, dry syrup, tablets, troches, granules, capsules, pills, suppositories, injection, ointment, dispersion, inhalant, suspension, solution, emulsion, syrup and elixir. The preparation may be in a unit dosage form e.g. tablets, troches, capsules, injection, vials, or granules or powder in a separate container or package.

Compounds I suitable for the said preparations and methods include the following preferable fluorohydroxyphenylmalonamido derivatives:

7β-[α-(2-fluoro-4-hydroxyphenyl)-α-carboxyacetamido]-7α-methoxy-3-(1-methyltetrazol-5-yl)thiomethyl-1-dethia-1-oxa-3-cephem-4-carboxylic acid and its sodium, potassium or calcium salt;

7β-[α-(2-fluoro-5-hydroxyphenyl)-α-carboxyacetamido]-7α-methoxy-3-(1-methyltetrazol-5-yl)thiomethyl-1-dethia-1-oxa-3-cephem-4-carboxylic acid and its sodium, potassium or calcium salt;

7β-[α-(2-fluoro-4-hydroxyphenyl)-α-carboxyacetamido]-7α-methoxy-3-(1,3,4-thiadiazol-5-yl)thiomethyl-1-dethia-1-oxa-3-cephem-4-carboxylic acid and its sodium or potassium salt;

7β-[α-(2-fluoro-5-hydroxyphenyl)-α-carboxyacetamido]-7α-methoxy-3-(1,3,4-thiadiazol-5-yl)thiomethyl-1-dethia-1-oxa-3-cephem-4-carboxylic acid and its sodium or potassium salt;

7β-[α-(2-fluoro-4-hydroxyphenyl)-α-carboxyacetamido]-7α-methoxy-3-(2-methyl-1,3,4-thiadiazol-5-yl)thiomethyl-1-dethia-1-oxa-3-cephem-4-carboxylic acid and its sodium or potassium salt; and 7β-[α-(2-fluoro-5-hydroxyphenyl)-α-carboxyacetamido]-7α-methoxy-3-(2-methyl-1,3,4-thiadiazol-5-yl)thiomethyl-1-dethia-1-oxa-3-cephem-4-carboxylic acid and its sodium or potassium salt, for the administration by injection;

7β-[α-(2-fluoro-4-hydroxyphenyl)-α-(5-indanyloxy)-carbonylacetamido]-7α-methoxy-3-(1-methyltetrazol-5-yl)thiomethyl-1-dethia-1-oxa-3-cephem-4-carboxylic acid, 7β-[α-(2-fluoro-5-hydroxyphenyl)-α-phenoxycarbonylacetamido]-7α-methoxy-3-(1-methyltetrazol-5-yl)thiomethyl-1-dethia-1-oxa-3 -cephem-4-carboxylic acid, 7β-[α-(2-fluoro-4-hydroxyphenyl)-α-(5-indanyloxy)-carbonylacetamido]-7α-methoxy-3-(1,3,4-thiadiazol-2-yl)thiomethyl-1-dethia-1-oxa-3-cephem-4-carboxylic acid, 7β-[α-(2-fluoro-5-hydroxyphenyl)-α-tolyloxycarboylacetamido]-7α-methoxy-3-(1,3,4-thiadiazol-2-yl)thiomethyl-1-dethia-1-oxa-3-cephem-4-carboxylic acid, 7β-[α-(2-fluoro-4-hydroxyphenyl)-α-phenoxycarbonylacetamido]-7α-methoxy-3-(2methyl-1,3,4-thiadiazol-5-yl)thiomethyl-1-dethia-1-oxa-3-cephem-4-carboxylic acid, 7β-[α-(2-fluoro-5-hydroxyphenyl)-α-(5-indanyloxy)-carbonylacetamido]-7α-methoxy-3-(2-methyl-1,3,4-thiadiazol-5-yl)-thiomethyl-1-dethia-1-oxa-3-cephem-4-carboxylic acid, and sodium or potassium salts thereof.

These salts may be mono- or di-salts or mixtures thereof including a neutral lyophilizate.

(3) SYNTHESIS

The compounds according to this invention can be prepared, for example, by one of the following methods:

(1) The reaction of Amine (II) or its reactive derivative with a haloarylmalonic acid (III) or its reactive derivative.

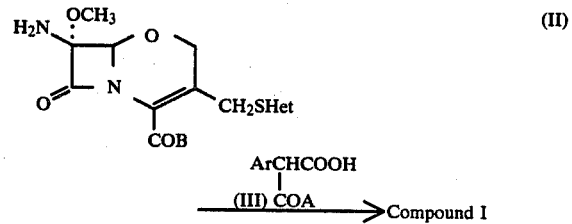

(in which Ar, COA, COB and Het are as defined above)

Said Amine II, 7β-amino-7α-methoxy-3-heteroaromatic thiomethyl-1-dethia-1-oxa-3-cephem-4-carboxylic acid derivative, is described as in Japanese Patent Unexamined Publication No. 51-33,401 and other literatures. The reactive derivatives of Amine II include those having 7-amino substituted or activated by silyl (e.g. trimethylsilyl, methoxydimethylsilyl), stannyl (e.g. trimethylstannyl), carbonyl, alkylene (e.g. enamino with acetone, acetylacetone, acetoacetic ester, acetoacetonitrile, acetacetamide, acetoacetanilide, cyclopentanedione or acetylbutyrolactone), alkylidene (e.g. benzylidene, 1-haloalkylidene, 1-haloaralkylidene, 1-alkoxyalkylidene or 1-alkoxy-1-phenoxyalkylidene), or acid (i.e. acid addition salt with a mineral acid, carboxylic acid, sulfonic acid or thiocyanic acid) or the like.

Haloarylmalonic acid III is a known substance or analogous substance to be derived from known substances by well-known methods.

COA is the same group as COA of Compound I, details of which are given above.

The reactive derivatives of the haloarylmalonic acid III include reactive esters, reactive amides, azides and the like.

This reaction can be carried out with the following seven types of reagents: (i) Free acid — This is used in the presence of a condensing reagent such as carbodiimide (e.g. N,N'-diethylcarbodiimide or N,N'-dicyclohexylcarbodiimide), carbonyl compound (e.g. carbonyldiimidazole), isoxazolinium salt, acylamino compound (e.g. 2-ethoxy-1-ethoxycarbonyl-1,2-dihydroquinoline) or the like reagent, preferably in an aprotic solvent e.g. halohydrocarbon, nitrile, ether, amide or the like, or mixtures thereof and preferably at a molar ratio of 1 to 2 of the free acid and 1 to 2 of the condensing reagent to the Amine II.

(ii) Acid anhydride—This can be a symmetrical or mixed anhydride (e.g. mixed anhydride with a mineral acid or alkoxyformic acid; mixed anhydride with an alkanoic acid, sulfonic acid or the like), intramolecular anhydride (e.g. ketene or isocyanide) or other anhydrides, which is available in the presence of an acid scavenger (e.g. inorganic base such as an oxide, hydroxide, carbonate or hydrogen carbonate of an alkali or alkaline earth metal; organic base such as triethylamine, N-methylmorpholine, N,N-dimethylaniline, pyridine or quinoline; oxirane such as ethylene oxide or propylene oxide; or aralkylene oxide such as styrene oxide), and preferably in an aprotic solvent (e.g. halohydrocarbon, nitrile, ether, amide solvents or a mixture thereof) at a preferable molar ratio of 1 to 2 of the acid anhydride and 1 to 10 of the acid scavenger to one of Amine II or its reactive derivative.

(iii) Acid halide—This is used preferably in the presence of the acid scavenger given in the preceding part (ii) in a solvent (e.g. halohydrocarbon, nitrile, ether, ketone, water or dialkylamide solvent, or a mixture thereof) at a molar ratio of 1 to 2 of the acid halide and 1 to 10 of the acid scavenger to 1 of Amine II or its reactive derivative.

(iv) Reactive ester—This can be of an enol ester (e.g. vinyl or isopropenyl ester, aryl ester (e.g. chlorophenyl, trichlorophenyl, pentachlorophenyl, dinitrophenyl or trinitrophenyl ester), heteroaromatic ester (e.g. an ester with 1-hydroxybenzotriazole) or ester with hydroxylamine, or the like.

(v) Reactive amide—This includes an aromatic amide e.g. an amide with imidazole, triazole, 3-oxo-benzoisothiazolidine 1,1-dioxide or 2-ethoxy-1,2-dihydroquinoline.

(vi) Formimino derivative—This includes, for example, and N,N-dimethylformimino ester.

(vii) Other reactive derivatives.

The reagents given in (iv) to (vi) above are subjected to the reaction, preferably in an aprotic solvent (e.g. halohydrocarbon, ether, ketone, amide or ester solvent, or mixtures thereof) at a molar ratio of one or more of the reactive derivative of haloarylmalonic acid III to 1 of Amine II or its reactive derivative.

(2) Treatment of a 7β-haloarylmalonamido-7α-methoxy-3-functionallized methyl-1-dethia 1-oxa-3-cephem-4-carboxylic acid or its derivative (IV) with a heteroaromatic thiol (V) or its reactive derivative.

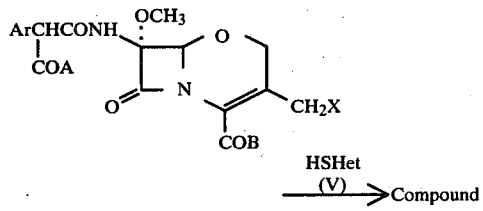

(wherein Ar, COA, COB and Het are as defined above and X is a functional group replaceble by the heteroaromatic thio group from Compound V).

Compound IV having chlorine, bromine, tosyloxy, mesyloxy, dichloroacetoxy or trifluoroacetoxy as X group can be made e.g. from a compound in which X group of Compound IV is replaced by acetoxy by subjecting to hydrolysis and successive halogenation or acylation.

Compound V is well-known in the art. The reactive derivatives of Compound V can be an alkali metal salt or a salt with an organic base e.g. triethylamine.

This reaction is carried out by treating the starting compound IV with said reagent V, preferably in an inert solvent (e.g. halohydrocarbon, ether, ketone or amide solvent), if required, in the presence of a base.

(3) The reaction of a 7β-haloarylmalonamido-3-epoxymethano-1-dethia-1-oxa-3-cephem-4-carboxylic acid derivative with Compound V or its reactive derivative or other nucleus formations including those analogous to the methods described in the references cited in the instant specification under "Background of This Invention".

(4) Introduction of 7α-methoxy into 7β-haloarylmalonamido-3-heteroaromatic thiomethyl-1-dethia-1-oxa-3-cephem-4-carboxylic acid or its derivative e.g. as follows:

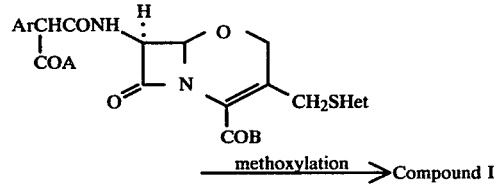

(wherein Ar, COA, COB, and Het are as defined above)

(a) Treatment with an N-halogenating reagent (e.g. t-butyl hypochlorite) and an alkali metal methoxide (e.g. sodium, potassium or lithium methylate) in methanol and subsequent reduction, when required;

(b) Treatment with t-butyl hypochlorite and methol base in tetrahydrofuran in the presence of e.g. phenyllithium, followed by, if required, reduction; and (c) Successive treatment with bromine-DBU, phosphorus pentachloride-pyridine, base, methanol-base, and trialkylsilyl chloride, in this order.

(5) When COA and/or COB is protected carboxy, the compound may be deprotected to give the corresponding free carboxylic acid. Representative deprotections include the following four:

(a) Highly reactive ester, amide, salt or anhydride for protection can be hydrolyzed by water with an acid or base or by a suitable aqueous buffer solution;

(b) Mild reductive removal of a haloethyl, benzyl, nitrobenzyl, methylbenzyl, dimethylbenzyl, diarylmethyl, triarylmethyl group or the like can be done under combination of an acid and a metal (e.g. zinc, tin or divalent chromium), by sodium dithionite or hydrogenation over e.g. platinum, palladium or nickel, to give said free carboxylic acid.

(c) Solvolysis of a benzyl, methoxybenzyl, methylbenzyl, dimethyoxybenzyl, t-alkyl, trityl, diarylmethyl, cyclopropylmethyl, sulfonylethyl or cyclopropylethyl ester with an acid (e.g. meneral acid, Lewis acid, sulfonic acid or strong carboxylic acid), if required together with a cation scavenger (e.g. anisole) giving the corresponding free acid.

(d) Removal of a phenacyl or ethinyl ester group with a base gives the free carboxy.

(6) Deprotection of RO as in a protected hydroxy group gives free hydroxy by conventional methods including the following:

(a) Reaction of acyloxy or hydrocarbyloxy (e.g. alkoxy or aralkoxy) with an acid (e.g. mineral acid, Lewis acid strong carboxylic acid or sulfonic acid as stated in above (5) (c)) preferably in the presence of a cation scavenger e.g. anisole, an inorganic base (e.g. hydroxide or carbonate of sodium or potassium) or an organic base: and (b) Hydrogenolytic deprotection of a benzyloxycarbonyl or benzyl group with hydrogen and platinum, palladium or nickel catalyst.

Reactions (5) and (6) may take place occasionally in the same treatment. Such parallel reactions are also included in the scope of both processes.

(7) Treatment of Compound I having free carboxy with an inorganic or organic base results in formation of a salt. Such as base salt can be of the corresponding hydroxide, weak carboxylic acid salt, carbonate, or salt with a weak acid, containing the objective metal in its cationic part. When a solid salt separates from an organic solvent, the salt formation in said solvent may be available for convenient purification of the product. Salts are also obtained conventionally by concentration of neutralized aqueous salt solution, lyophilization or other methods.

These reactions can be carried out at about $-30°$ C. to $100°$ C., preferably at $-20°$ C. to $50°$ C. The reaction solvent may further be selected from halohydrocarbons (e.g. dichloromethane, chloroform, dichloroethane, trichloroethane or chlorobenzene), ethers (e.g. diethyl ether, tetrahydrofuran, tetrahydropyran, dimethoxyethane or anisole), ketones (e.g. acetone, methyl ethyl ketone, methyl isobutyl ketone, cyclohexanone or acetophenone), esters (e.g. ethyl acetate, butyl acetate or methyl benzoate), nitrohydrocarbons, nitriles (e.g. acetonitrile or benzonitrile), amides (e.g. formamide, acetamide, dimethylformamide, dimethylacetamide, hexamethylphosphorotriamide or caprolactam), sulfoxides (e.g. dimethyl sulfoxide), acids (e.g. formic or acetic acid), bases (e.g. butylamine, triethylamine, pyridine, picoline or quinoline), water, and the like, or the mixtures thereof.

If required, the reaction is accelerated by stirring, protected from air by using an inert gas stream or kept dry by using conventional measures for exclusion of moisture.

The product can be obtained, for example, after removing solvents, by-products and unreacted starting materials in a conventional manner (e.g. concentration, extraction, absorption, elution or washing) and it is purified in a conventional manner (e.g. reprecipitation, chromatography, recrystallization or other purifying methods).

WORKING EXAMPLES

The following examples are given to show in detail some specific embodiments of this invention.

In the formulae and tables, the following abbreviations are used:

Ac=acetyl, ANS=anisyl, BH=diphenylmethoxycarbonyl,
ET=ethyl, MeTdz=2-methyl-1,3,4-thiadiazol-5-yl,
Ph=phenyl, PMB=anisyloxycarbonyl, Tdz=1,3,4-thiadiazol-2-yl, Tetr=1-methyltetrazol-5-yl, and Temp.=temperature.

EXAMPLE 1

(Acylation)

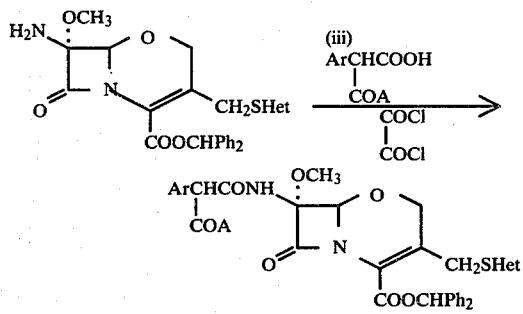

(wherein Ar, COA and Het are as defined above)

Haloarylmalonic acid (iii) is dissolved in dichloromethane. Triethylamine and oxalyl chloride are added thereto at −20° C. The mixture is warmed to 0° C. and stirred for a determined period of time to give a solution of the corresponding haloarylmalonic acid chloride. This is added to a solution of Amine (ii) in dichloromethane basified with pyridine with stirring under cooling. The mixture is cooled for a while at e.g. +10° to −20° C. and then poured into dilute hydrochloric acid or dilute phosphoric acid. The mixture is extracted with dichloromethane or ethyl acetate. The extract solution is washed with water, dried and concentrated under reduced pressure. The obtained residue is chromatographed over silica gel. Benzene-ethyl acetate eluates give the objective compound (i).

Used reaction conditions are listed in Table 1 and obtained physical constants of the products are given in Table 2.

Detailed procedure of Experiment No. 5 is shown below representing the procedures of experiments in Table I.

(No. 5) To a solution of α-(2-fluoro-4-hydroxyphenyl)-α-diphenylmethoxycarbonylacetic acid (456 mg=1.2 mmoles) in dichloromethane (4 ml) are added triethylamine (0.14 ml−1 mmole) and oxalyl chloride (86 μg=1 mmole) under ice-cooling. After stirring for 1 hour, the solution is added to a solution of diphenylmethyl 7β-amino-7α-methoxy-3-(1-methyltetrazol-5-yl)thiomethyl-1-dethia-1-oxa-3-cephem-4-carboxylate (204 mg) in a mixture of dichloromethane (4 ml) and pyridine (100 μl=1.2 mmole). The mixture is stirred for 50 minutes under ice-cooling. The reaction mixture is poured into 5% aqueous phophoric acid and extracted with ethyl acetate. The extract is washed with water, dried over sodium sulfate and concentrated in vacuo. The obtained residue is chromatographed over silica gel to give dipheylmethyl 7β-[-(4-hydroxy-2-fluorophenyl)-α-diphenylmethoxycarbonylacetamido]-7α-methoxy-3-(1-methyltetrazol-5-yl)thiomethyl-1-dethia-1-oxa-3-cephem-4-carboxylate (Compound 5) (180mg=51.7% yield) in an amorphous state.

EXAMPLE 2

(Deprotection)

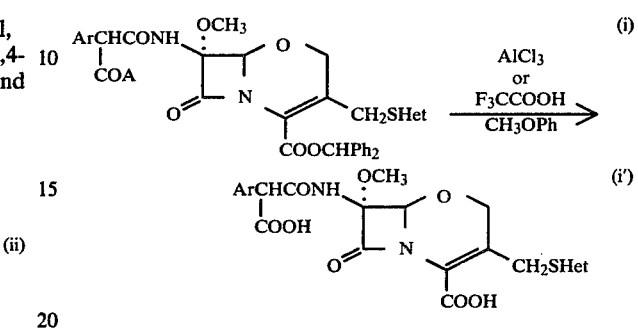

(wherein Ar, COA and Het are as defined above)

Diphenylmethyl 7β-(α-haloaryl-α-protected carboxyacetamido)-7α-methoxy-3-heteroaromatic thiomethyl-1-dethia-1-oxa-3-cephem-4-carboxylate (i) is dissolved in dichloromethane and/or anisole. Trifluoroacetic acid or a solution of aluminum chloride in nitromethane is added thereto and stirred at about 0° C.

When trifluoroacetic acid is used, the reaction mixture is concentrated in vacuo, triturated with ether to give solid product, which is separated and kept in vacuo to remove the remaining solvent, giving 7β-(α-haloaryl-α-carboxyacetamido)-7α-methoxy-3-heteroaromatic thiomethyl-1-dethia-1-oxa-3-cephem-4-carboxylic acid (i').

When aluminum chloride in nitromethane is used, the reaction mixture is diluted with ethyl acetate, washed with hydrochloric acid and extracted with aqueous hydrogencarbonate. The aqueous extract is acidified to pH 1.5 and reextracted with ethyl acetate. The extract solution is concentrated. The obtained residue is triturated in a solvent to give objective free carboxylic acid (i').

Utilized reaction conditions are listed in Table 3 and the physical constants of the products of Table 3 are shown in Table 4.

Detailed procedure of Experiment No. 15 is given below, representing the procedures of experiments in Table 3.

(No. 15) To a solution of diphenylmethyl 7β-[α-(4-methoxybenzyloxy-2-fluorophenyl)-α-diphenylmethoxycarbonylacetamido]-7α-methoxy-3-(1-methyltetrazol-5-yl)thiomethyl-1-dethia-1-oxa-3-cephem-4-carboxylate (10 g) in anisole (20 ml) at −5° C. is added trifluoroacetic acid (20 ml), and the mixture is stirred at the same temperature for 30 minutes and concentrated in vacuo. The residue is stirred with ether (100 ml), mixed with petroleum ether, and stirred. The precipitated powder is collected by filtration to give 7β-[α-(2-fluoro-4-hydroxyphenyl)-α-carboxyacetamido]-7α-methoxy-3-(1-methyltetrazol-5-yl)-thiomethyl-1-dethia-1-oxa-3-cephem-4-carboxylic acid (5.44 g=100% yield).

The p-methoxybenzyl at the 4 position of haloaryl and the diphenylmethyl carboxy-protecting group are deprotected in the said treatment to give both of free hydroxy and free carboxy, respectively.

EXAMPLE 3

(Salt Formation)

(1) To a solution of 7β-[α-(4-hydroxy-2-fluorophenyl)-α-carboxyacetamido]-7α-methoxy-3-(1-methyltetrazol-5-yl)thiomethyl-1-dethia-1-oxa-3-cephem-4-carboxylic acid (14.9 g) in methanol (60 ml) is added dropwise a solution of sodium 2-ethylhexanoate (0.138 mole) in methanol (69 ml), and the mixture is diluted dropwise by addition of ethyl acetate (650 ml) to the mixture over a 10 minute period. The precipitated crystals are collected by filtration, washed with ethyl acetate and ether, and dried to give the corresponding disodium salt (11.1 g=68.1% yield).

IR: $\lambda_{max}^{Nujol}$ 3175, 1770, 1680, 1610, 1501 cm$^{-1}$.
NMR: $\delta^{D2O}$ (3.50s+3.55s)3H, (4.01+4.25)ABq(13Hz)2H, 4.00s3H, 4.50brs2H, (5.10+5.13s)1H, 6.47–7.47m3H.

(2) Said compounds I having free carboxy at the 4 position are dissolved in aqueous sodium hydrogen carbonate to give a solution of their sodium salt, diluted to a required concentration, buffered to pH 7 and assayed on an agar plate according to a conventional manner. They show high antibacterial activities against various strains of gram negative and positive bacteria.

The preparations 1–3 which follow Examples 4 and 5 are given to show the method for preparing Haloarylmalonic acid (III) or its reactive derivatives for the synthesis.

EXAMPLE 4

(Injection)

A solution of a neutral lyophilizate 7β-[α-(2-fluoro-4-hydroxyphenyl)-α-carboxyacetamido]-7α-methoxy-3-(1-methyltetrazol-5-yl)thiomethyl-1-dethia-1-oxa-3-cephem-4-carboxylic acid sodium salt (0.2 g) in physiological saline (100 ml) is dripped into a patient suffering from urinary tract infection caused by Serratia marsescens and Escherichia coli.

EXAMPLE 5

(Tablets)

Two 250 mg capsules each containing crystals of 7β-[α-(2-fluoro-5-hydroxyphenyl)-α-phenoxycarbonylacetamido]-7α-methoxy-3-(1-methyltetrazol-5-yl)thiomethyl-1-dethia-1-oxa-3-cephem-4-carboxylic acid (0.2 g), corn starch (0.05 g) and magnesium stearate (0.01 g) is given twice a day to a patient suffering from upper inspiratory tract infection caused by Klebsiella pneumoniae.

Preparation 1

To a solution of 4-hydroxy-2-fluorophenylacetic acid in methylene chloride is added dropwise a solution of diphenyldiazomethane in n-hexane. A small amount of glacial acetic acid is added thereto. The mixture is concentrated to give the corresponding diphenylmethyl ester. The product is dissolved in acetone, and 1.3 equivalents of p-methoxybenzyl chloride, 1.2 equivalents of sodium iodide and 1.2 equivalents of potassium carbonate are added thereto. The mixture is stirred at 50° C. for 12 hours and, after removal of inorganic compounds, is extracted with ethyl acetate. The extract is concentrated and the residue is crystallized from methanol to give diphenylmethyl 4-p-methoxybenzyloxy-2-fluorophenylacetate. A mixture of a solution of n-butyllithium in hexane (2.3 mole/liter=45.13 ml), diisopropylamine (14.55 ml) and tetrahydrofuran (250 ml) is stirred at −5° C. for 10 minutes. A solution of the above product (23.7 g) in tetrahydrofuran is added thereto at −55° C. The mixture is stirred at −55° C. for 30 minutes and then warmed to 0° C. after adding powder of dry ice. The mixture is evaporated to remove the solvent. The residue is dissolved in ethyl acetate and washed with ice-water and 10% hydrochloric acid (85 ml). The organic layer is washed, dried and evaporated to give monobenzhydryl 4-p-methoxybenzyloxy-2-fluorophenylmalonate (27 g).

NMR: $\delta_{ppm}^{CDCl3}$ 3.78s3H, 4.93s2H, 5.00s1H, 6.87s1H, 6.46–7.35m7H.

TLC: Rf=0.43 (ethyl acetate/silica gel plate)

In a similar manner, monobenzhydryl 2-p-methoxybenzyloxy-4-fluorophenylmalonate can be prepared by substituting 4-hydroxy-2-fluorophenylacetic acid with 2-hydroxy4-fluorophenyacetic acid.

Preparation 2 p-Chlorophenylacetonitrile is prepared by the reaction of p-chlorobenzyl chloride and sodium cynide in dimethyl sulfoxide, and is refluxed with sodium hydroxide in ethanol to give p-chlorophenylacetic acid. The acid is esterified with diphenyldiazomethane to give diphenylmethyl p-chlorophenylacetate (mp. 107°–108° C.). The ester (1 g) is dissolved in tetrahydrofuran. To this solution is added dropwise a solution of dissopropylamine (1.04 ml) and n-butyllithium (0.48 g) in a mixture of hexane and tetrahydrofuran (20 ml). The mixture is stirred at −10° C. for 20 minutes and for additional 1.5 hours after adding dry ice. The reaction mixture is mixed with 10% hydrochloric acid under cooling and extracted with ethyl acetate. The extract is washed with water, dried and evaporated. The residue is recrystallized from benzene to give monobenzhydryl 4-chlorophenylmalonate (942 mg = 83% yield). m.p. 138°–139° C.

IR: $\lambda_{max}^{nujol}$ 3200, 1745, 1710 cm$^1$.
NMR: $\delta_{ppm}^{CDCl3}$ 4.17s1H, 4.70s1H. 6.87s1H, 7.2–7.4ml 4H.

In similar manner, monobenzyhydryl 2-chlorophenylmalonate, monobenzhydryl 3-chlorophenylmalonate and monobenzhydryl 2-fluorophenylmalonate are obtained by substituting p-chlorophenylacetonitrile with o-chlorophenylacetonitrile, m-chlorophenylacetonitrile and o-fluorophenyacetonitrile, respectively.

Preparation 3

Under ice-cooling, monoethyl oxalate monochloride (10.5 g) is added dropwise to a solution of aluminum chloride (10.5 g) in nitrobenzene (30 ml). To the solution is added dropwise 2-chloro-5-fluoroanisole (84 g). After 30 minutes, the mixture is poured into ice-water and extracted with ether. The extract is washed with dilute hydrochloric acid and dilute aqueous sodium bicarbonate, dried and evaporated to remove the solvent. Recrystallization from a mixture of ether and n-hexane gives ethyl 4-methyl-3-chloro-6-fluorophenylglyoxalate (mp. 84°–85° C.). A mixture of the glyoxalate (5.21 g), ethylene glycol (28 ml), potassium hydroxide (4.5 g) and hydrazine monohydrate (2.85 ml) is heated at 155°–158° C. for 1.5 hours and then at 220° C. for 2 hours and poured into water. The mixture is washed with ether, acidified with hydrochloric acid and extracted with ether. The extract is evaporated. The obtained residue is recrystallized from dichloromethane to give 3-chloro-4-hydroxy-6-fluorophenylacetic acid (mp. 137°–138° C.). A part of the acid (0.615 g) is suspended in dichloromethane (15 m) and esterified with diphenyldiazomethane to give crystals of the corresponding diphenylmethyl ester (mp. 121°–122° C.).

The ester (371 mg) is dissolved in tetrahydrofuran (1 ml) and poured into a mixture of diisopropylamine (0.56 ml), tetrahydrofuran (20 ml) and a solution of n-butyllithium in hexane (1.6 M; 2.5 ml) at −60° C. The mixture is stirred at −60° C. to −20° C. for 20 minutes, cooled to −60° C., and mixed with dry ice. After 10 minutes, the reaction mixture is warmed to room temperature and stirred for 20 minutes at the same temperature. The solvent is evaporated in vacuo. To the obtained residue is added ice-water and ethyl acetate. The mixture is acidified to pH 3 with 10% hydrochloric acid. The organic layer is separated, washed with water, dried, and concentrated under reduced pressure. The residue is crystallized from a mixture of benzene and hexane to give diphenylmethyl 3-chloro-6-fluoro-4-hydroxyphenylmalonate (365 mg=88% yield). mp. 100°–103° C.

NMR: $\delta_{ppm}^{CDDCl_3}$ 4.94s, 6.69d(J=10.5Hz)1H, 6.89s1H, 7.1–7.5m1H.

Table 1

Scheme: H₂N-[β-lactam with OCH₃, CH₂SHet, COOCHPh₂] (ii) + ArCHCOOH/COA (iii) →[COCl-COCl] ArCHCONH-[β-lactam with OCH₃, CH₂SHet, COOCHPh₂]/COA (i); Het = pyridyl group shown.

| Ex. No. | Haloarylmalonic acid (iii) Ar | COA | (mg) | Acylation conditions CH₂Cl₂ (ml) | NEt₃ (μl) | (μl) | Temp (°C.) | Time (min) | Amine (ii) Het | (mg) | (μl) | CH₂Cl (ml) | Temp (°C.) | Time (min) | Product (i) No. | (mg) | % |
|---|---|---|---|---|---|---|---|---|---|---|---|---|---|---|---|---|---|
| 1 | 2-F-C₆H₃-Me | BH | 145 | 4 | 42 | 26 | −20, 0 | 60 | Tetr | 102 | 24 | 5 | 0 | 30 | 1 | 150 | 86 |
| 2 | 2-Cl-C₆H₃-Me | " | 153 | 4 | 42 | 26 | −20, 0 | 60 | " | 102 | 24 | 5 | 0 | 30 | 2 | 170 | 97 |
| 3 | 3-Cl-C₆H₃-Me | " | 164 | 2 | 42 | 26 | 0 | 35 | " | 102 | 24 | 5 | 0 | 90 | 3 | 167 | 96 |
| 4 | 4-Cl-C₆H₃-Me | " | 152 | 2 | 42 | 26 | 0 | 30 | " | 102 | 24 | 5 | 0 | 50 | 4 | 181 | — |
| 5 | 3-F-4-HO-C₆H₂-Me | " | 456 | 4 | 140 | 86 | 0 | 60 | " | 204 | 100 | 4 | 0 | 50 | 5 | 180 | 52 |
| 6 | 3-F-4-ANSO-C₆H₂-Me | " | 27000 | 160 | 5620 | 3450 | −15, 0 | 60 | " | 1370 | 3260 | 400 | −3, 0 | 30 | 5' | 26150 | 98 |
| 7 | 2-F-4-HO-C₆H₂-Me | " | 152 | 2 | 42 | 26 | 0 | 45 | " | 102 | 24 | 4 | −10, 0 | 150 | 6 | 75 | — |
| 8 | 3-Cl-4-HO-C₆H₂-Me | BH | 159 | 2 | 42 | 26 | 0 | 120 | Tetr | 102 | 24 | 5 | −20 | 120 | 7 | 111 | 63 |
| 9 | 2-Cl-4-HO-C₆H₂-Me | " | 159 | — | — | 26 | 0 | — | " | 102 | 40 | 5 | 0 | 90 | 8 | 102 | 58 |

Table 1-continued

Acylation conditions $$\underset{(ii)}{\underset{H_2N}{\overset{OCH_3}{\vphantom{O}}}\text{-}\beta\text{-lactam-CH}_2\text{SHet, COOCHPh}_2} \xrightarrow[\underset{COCl}{COCl}]{\underset{(iii)\ ArCHCOOH}{COA}} \underset{(i)}{\underset{ArCHCONH}{\overset{OCH_3}{\vphantom{O}}}\text{-}\beta\text{-lactam-CH}_2\text{SHet, COOCHPh}_2}$$

Amine (ii) Het = pyridine-type

| Ex. No. | Haloarylmalonic acid (iii) Ar | COA | (mg) | CH₂Cl₂ (ml) | NEt₃ (μl) | COCl-COCl (μl) | Temp (°C) | Time (min) | Amine (ii) Het | (mg) | Pyridine (μl) | CH₂Cl₂ (ml) | Temp (°C) | Time (min) | Product (i) No. | (mg) | % |
|---|---|---|---|---|---|---|---|---|---|---|---|---|---|---|---|---|---|
| 10 | CF₃-CH₃-HO-phenyl | " | 344 | 4 | 84 | 52 | 0 | 60 | " | 102 | 48 | 5 | 0 | 20 | 9 | 99 | 54 |
| 11 | F-CH₃-HO-phenyl | " | 380 | 5 | 111 | 68 | 0 | 40 | " | 204 | 81 | 10 | 0 | 40 | 10 | 196 | 56 |
| 12 | OANS-CH₃-HO-phenyl | " | 400 | 2 | 93 | 57 | 0 | 60 | " | 138 | 65 | — | 0 | 60 | 11 | 228 | 86 |
| 13 | F-CH₃-HO-F-phenyl | " | 257 | — | 70 | 45 | 0 | — | " | 102 | 40 | 4 | 0 | 150 | 12 | 92 | 51 |
| 14 | Cl-CH₃-HO-Cl-phenyl | " | 346 | — | 84 | 52 | 0 | 60 | " | 102 | 48 | 5 | 0 | 30 | 13 | 118 | 64 |
| 15 | Cl-CH₃-HO-Cl-phenyl | " | 172 | — | 42 | 26 | 0 | — | " | 102 | 24 | 5 | −20 | 45 | 14 | 92 | 50 |
| 16 | F-CH₃-HO-phenyl | BH | 202 | 5 | 56 | 34 | 0 | 60 | Tdz | 100 | 45 | 5 | −40 | 20 | 15 | 105 | — |
| 17 | ANSO-phenyl | " | 202 | — | 56 | 34 | 0 | 60 | MeTdz | 105 | 45 | 5 | −30 | 30 | 16 | 145 | — |

Table 1-continued

Acylation conditions $$\underset{(ii)}{\overset{OCH_3}{\underset{H_2N}{\vphantom{|}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!} \;+\; \underset{COCl}{\overset{COCl}{\underset{(iii)\;ArCHCOOH}{COA}}} \longrightarrow \underset{(i)}{\overset{OCH_3}{ArCHCONH\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!}}$$

| Ex. No. | Haloarylmalonic acid (iii) Ar | COA | (mg) | CH$_2$Cl$_2$ (ml) | NEt$_3$ (μl) | COCl–COCl (μl) | Temp (°C.) | Time (min) | Amine (ii) Het | (mg) | CH$_2$Cl$_2$ (ml) | Pyridine (μl) | Temp (°C.) | Time (min) | Product (i) No. | (mg) | % |
|---|---|---|---|---|---|---|---|---|---|---|---|---|---|---|---|---|---|
| 18 | ![F, CH3 aryl] | PMB | 182 | 5 | 56 | 32 | 0 | 60 | Tdz | 100 | 4 | 45 | 0 | 30 | 17 | 145 | — |
| 19 | ANSO— " | " | 182 | — | 42 | 26 | 0 | 60 | MeTdz | 105 | 5 | 33 | −30 | 30 | 18 | 125 | — |

Table 2

Physical constants of Products (i)

$$\text{ArCHCONH} \begin{array}{c} \text{OCH}_3 \\ | \end{array} \cdots \text{(β-lactam structure)} \cdots \text{CH}_2\text{SHet}$$

Structure (i): ArCH(COA)CONH- attached to β-lactam with OCH₃, fused to ring with N, COOCHPh₂, CH₂SHet substituents.

| No. | Ar | COA | Het | State | IR: $\nu_{max}^{CHCl_3}$ (cm$^{-1}$) | NMR: $\delta_{ppm}^{CDCl_3}$ (Hz values show coupling constants.) | TLC: Rf/SiO₂ (PhH+EtOAc) |
|---|---|---|---|---|---|---|---|
| 1 | 2-F-phenyl | BH | Tetr | foam | 1792, 1726. | 3.43s3H, 3.50s3H, 4.17s2H, 4.45s2H, 4.98s1H, 5.00brs1H, 6.87s1H, 6.90s1H, 7.0-8.0m25H. | — |
| 2 | 2-Cl-phenyl | " | " | " | 1791, 1726. | (3.40s+3.43s)3H, 3.57s3H, 4.17s2H, 4.42s2H, 4.93s1H, (5.13s+5.20s)1H, 6.83s1H, 6.87s1H, 7.0-8.0m25H. | — |
| 3 | 3-Cl-phenyl | " | " | " | 1790, 1725, 1700sh | 3.40s3H, 3.67s3H, 4.18s2H, 4.45s2H, 4.72s1H, 5.00split1H, 6.87s1H, 6.90s1H, 7.0-7.6m24H. | 0.5 (2:1) |
| 4 | 4-Cl-phenyl | " | " | powder | 1790, 1730. | 3.38s3H, 3.63s3H, 4.17s2H, 4.43s2H, 4.73s1H, 4.97s1H, 6.87s1H, 6.90s1H, 7.0-7.6m24H. | 0.16 (5:1) |
| 5 | 3-F-4-HO-phenyl | " | " | foam | — | 3.47s3H, (3.67+3.70s)3H, 4.13brs2H, 4.40brs2H, 4.87s1H, 4.98s1H, 6.23-7.73m. | — |
| 5' | 3-F-4-ANSO-phenyl | " | " | " | 1790, 1720, 1625, 1510, 1500. | 3.47s3H, 3.75s3H, 3.78s3H, 4.23brs2H, 4.50brs2H, 4.93brs1H, 4.97s2H, 5.00s1H, 6.87s1H, 6.90s1H, 6.6-7.0m4H, 7.15-7.7m24H. | 0.49 (2:1) |
| 6 | 2-F-4-HO-phenyl | " | " | " | 1790, 1730, 1720. | 3.45s3H, (3.70+3.73s)3H, 4.17brs2H, 4.43brs2H, 4.63s1H, 5.00s1H, 6.87s1H, 6.90s1H, 6.6-8.1m24H. | 0.48 (1:1) |
| 7 | 3-Cl-4-HO-phenyl | " | " | " | 1790, 1725. | 3.35s3H, (3.68s+3.70s)3H, 3.98brs2H, 4.46brs2H, 4.98s1H, (5.05s+5.10s)1H, 6.4-7.6m. | 0.46 (1:1) |
| 8 | 2-Cl-4-HO-phenyl | " | " | " | 1790, 1725. | 3.47s3H, (3.76s+3.78s)3H, 4.23brs2H, 4.50brs2H, 4.64s1H, (5.02s+5.04s)1H, 6.7-7.6m. | 0.52 (1:1) |
| 9 | 3-CF₃-4-HO-phenyl | " | " | " | 1792, 1725br. | 3.52s3H, 3.77s3H, 4.17brs2H, 4.50brs2H, 5.03s1H, 5.07s1H, 6.87s1H, 6.93s1H, 7.0-7.83m24H. | 0.45 (1:1) |
| 10 | 2-F-5-HO-phenyl | " | " | powder | 3570, 1790, 1725. | 3.47s3H, 3.78s3H, 4.22s2H, 4.48s2H, 5.00s1H, 5.03s1H, 6.8-7.7m25H. (CDCl₃+CD₃OD) | 0.20 (2:1) |
| 11 | 2-OANS-5-F-phenyl | " | " | foam | — | (3.32s+3.38s)3H, 3.65s6H, 4.17brs2H, 4.42brs2H, 4.73brs2H, 4.97m2H, 6.3-7.9m. | — |
| 12 | 2-Cl-4-HO-5-F-phenyl | " | " | powder | 1790, 1725. | (3.45s+3.47s)3H, 3.69s3H, 4.19brs2H, 4.49brs2H, 4.89brs1H, (5.00s+5.03s)1H, 6.59d(10.5Hz)1H, 6.83s1H, 6.90s1H, 7.0-7.7m21H. | 0.51 (1:1) |
| 13 | 2,3-Cl₂-4-HO-phenyl | " | " | " (mp.118° C.) | 1791, 1725. | 3.53s3H, 3.77s3H, 4.20s2H, 4.50s2H, 5.00s1H, (5.07s+5.12s)1H, 6.86s1H, 6.88s1H, 6.97-8.0m23H. | 0.48 (1:1) |
| 14 | 3,5-Cl₂-4-HO-phenyl | " | " | foam | 1785, 1720. | (3.52+3.56s)3H, (3.72+3.73s)3H, 4.27s2H, 4.59brs2H, 5.10s2H, 6.90s1H, 6.93s1H, 6.98s1H. | 0.35 (2:1) |

Table 2-continued

Physical constants of Products (i)

$$\text{ArCHCONH} \underset{\text{COA}}{\overset{\text{OCH}_3}{\mid}} \text{-[β-lactam ring]- CH}_2\text{SHet, COOCHPh}_2 \quad (i)$$

| No. | Ar | COA | Het | State | IR: $\nu_{max}^{CHCl_3}$ (cm$^{-1}$) | NMR: $\delta_{ppm}^{CDCl_3}$ (Hz values show coupling constants.) | TLC: Rf/SiO$_2$ (PhH+EtOAc) |
|---|---|---|---|---|---|---|---|
| 15 | F / ANSO (on benzene) | BH | Tdz | foam | 1790, 1728, 1613, 1497, 1252. | 3.46brs3H, 3.77s3H, (4.93+4.56)ABq(8Hz)2H, 4.50s2H, 4.82s2H, 4.98split1H, 5.02s1H, 6.78–7.75m31H. | — |
| 16 | " | " | MeTdz | " | 3420, 1787, 1723, 1610, 1495, 1248 | 2.53s3H, 3.47brs3H, 3.72s3H, 4.2–4.58m4H, 4.82s2H, 5.02s1H, 5.08s1H, 6.93s2H, 6.78–7.93m28H. | — |
| 17 | F / ANSO (on benzene) | PMB | Tdz | " | 3400, 1790, 1725, 1625, 1615. | 3.43s3H, 3.73s6H, (4.20+4.53)ABq2H, 4.47s2H, 4.83s1H, 4.87s2H, 4.97s1H, 5.07s2H, 6.43–7.67m21H, 8.83s1H. | — |
| 18 | " | " | MeTdz | " | 3410, 1781, 1720, 1245. | 2.60s3H, 3.48s3H, 3.73s3H, 3.77s3H, (4.25–4.60)m4H, 4.87s1H, 4.93s2H, 5.02s1H, 5.13s2H, (6.53–7.65)m23H. | — |

Table 3

Deprotection conditions $$(i) \xrightarrow{\text{acid}} (i')$$

where (i) has COA/COOCHPh$_2$ and (i') has COOH/COOH.

| Ex. No. | Compound (i) Ar | COA | Het | (mg) | CH$_2$Cl$_2$ (ml) | CH$_2$OPh (μl) | acid (mg) | Solvent (ml) | Temp. (°C.) | Time (min) | Product (i') No. | (mg) | % |
|---|---|---|---|---|---|---|---|---|---|---|---|---|---|
| 1 | F (o-) | BH | Tetr | 148 | 2.5 | 110 | AlCl$_3$ (113) | CH$_3$NO$_2$(1.4) | 0 | 20 | 19 | 63 | 71 |
| 2 | Cl (o-) | " | " | 165 | 2.5 | 120 | AlCl$_3$ (124) | CH$_3$NO$_2$(1.5) | 0 | 20 | 20 | 78 | 77 |
| 3 | Cl (m-) | " | " | 155 | 3 | 300 | CF$_3$COOH (300) | — | 0 | 50 | 21 | 87 | 90 |
| 4 | Cl (p-) | " | " | 173 | 3 | 300 | CF$_3$COOH (300) | — | 0 | 70 | 22 | 63 | 59 |
| 5 | F, HO (on benzene) | " | " | 180 | 0 | 400 | CF$_3$COOH (400) | — | 0 | 30 | 23 | 111 | 100 |
| 6 | F, HO (on benzene) | " | " | 75 | 1.5 | 300 | CF$_3$COOH (300) | — | 0 | 40 | 24 | 33 | — |
| 7 | Cl, HO (on benzene) | " | " | 108 | 2 | 400 | CF$_3$COOH (400) | — | 0 | 35 | 25 | 64 | 96 |
| 8 | Cl, HO (on benzene) | " | " | 102 | 2 | 400 | CF$_3$COOH (400) | — | 0 | 40 | 26 | 47 | 74 |

Table 3-continued

Deprotection conditions $$\text{ArCHCONH} \begin{array}{c} \text{OCH}_3 \\ | \\ \text{COA} \end{array} \begin{array}{c} O \\ \| \\ N \end{array} \begin{array}{c} O \\ | \\ \text{CH}_2\text{SHet} \\ | \\ \text{COOCHPh}_2 \end{array} \xrightarrow{\text{acid}} \text{ArCHCONH} \begin{array}{c} \text{OCH}_3 \\ | \\ \text{COOH} \end{array} \begin{array}{c} O \\ \| \\ N \end{array} \begin{array}{c} O \\ | \\ \text{CH}_2\text{SHet} \\ | \\ \text{COOH} \end{array}$$

(i) → (i')

| Ex. No. | Compound (i) Ar | COA | Het | (mg) | CH₂Cl₂ (ml) | CH₂OPh (μl) | acid (mg) | Solvent (ml) | Temp. (°C.) | Time (min) | Product (i') No. | (mg) | % |
|---|---|---|---|---|---|---|---|---|---|---|---|---|---|
| 9 | 4-F, 3-HO-phenyl | " | " | 192 | 3 | 300 | CF₃COOH (300) | — | 0 | 35 | 28 | 107 | 90 |
| 10 | 2-OH, 5-F-phenyl | " | " | 228 | 5 | 350 | CF₃COOH (400) | — | 0 | 40 | 29 | 110 | 89 |
| 11 | 3-F, 5-HO, 4-Cl-phenyl | " | " | 88 | 2 | 400 | CF₃COOH (400) | — | 0 | 40 | 30 | 55 | 99 |
| 12 | 2,3-Cl₂, 4-HO-phenyl | " | " | 115 | 2 | 400 | CF₃COOH (400) | — | 0 | 30 | 31 | 57 | 78 |
| 13 | 3,5-Cl₂, 4-HO-phenyl | " | " | 90 | 2 | 300 | CF₃COOH (300) | — | 0 | 20 | 32 | 46 | 80 |
| 14 | 2-CF₃, 4-HO-phenyl | " | " | 96 | 2 | 400 | CF₃COOH (400) | — | 0 | 30 | 27 | 62 | 100 |
| 15 | 2-F, 4-ANSO-phenyl | " | " | 10 (g) | 0 | 20 (ml) | CF₃COOH (20ml) | — | −5 | 30 | 23 | 5.44 (g) | 100 |
| 16 | 2-F, 4-ANSO-phenyl | " | Tdz | 105 | 0 | 300 | CF₃COOH (300) | — | 0 | 30 | 33 | 35 | — |
| 17 | " | " | MeTdz | 145 | 0 | 350 | CF₃COOH (350) | — | 0 | 30 | 34 | 50 | — |
| 18 | 2-F, 4-ANSO-phenyl | PMB | Tdz | 145 | 0 | 1000 | CF₃COOH (1000) | — | 0 | 30 | 35 | 75 | 91 |
| 19 | " | " | MeTdz | 125 | 0 | 250 | CF₃COOH (250) | — | 0 | 30 | 36 | 40 | — |

Table 4

Physical constants of Products (i')

$$\text{ArCHCONH} \begin{array}{c} \text{OCH}_3 \\ | \\ \text{COOH} \end{array} \begin{array}{c} O \\ \| \\ N \end{array} \begin{array}{c} O \\ | \\ \text{CH}_2\text{SHet} \\ | \\ \text{COOH} \end{array} \quad (i')$$

| Compound (i') No. | Ar | Het | State | IR: $\nu_{max}^{CHCl_3}$ (cm⁻¹) | NMR: $\delta_{ppm}^{CDCl_3}$ (Hz values show coupling constants) | TLC: Rf/SiO₂ (EtOAc+HOAc+H₂O) |
|---|---|---|---|---|---|---|
| 19 | 2-F-phenyl | Tetr | powder (m.p. 44° C.) | 3350, 1785, 1720, 1635 | — | 0.5 (5:1:1) |

Table 4-continued

Physical constants of Products (i')

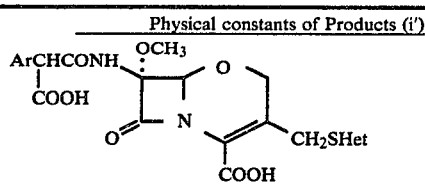

(i')

| Compound (i') | | | | | |
|---|---|---|---|---|---|
| No. | Ar | Het | State | IR:$\nu_{max}^{CHCl_3}$ (cm$^{-1}$) | NMR:$\delta_{ppm}^{CDCl_3}$ (Hz values show coupling constants) | TLC:Rf/SiO$_2$ (EtOAc+HOAc +H$_2$O) |

| No. | Ar | Het | State | IR | NMR | TLC |
|---|---|---|---|---|---|---|
| 20 | 2-Cl, Me-C$_6$H$_3$ | " | powder (m.p.127° C.) | 3250,1789,1724. | — | 0.6 (5:1:1) |
| 21 | 3-Cl, Me-C$_6$H$_3$ | " | powder | 1785,1720,1630. | — | 0.26 (8:1:1) |
| 22 | 4-Cl, Me-C$_6$H$_3$ | " | " | 1785,1720,1635. | — | 0.2 (8:1:1) |
| 23 | 3-F, 4-HO-C$_6$H$_3$ | " | " | 3300,1780,1725, 1625,1600,1513. | (3.47+3.53s)3H,3.93s3H,4.27brs2H,4.53brs 2H,5.05s1H,6.33-7.53m3H. (CDCl$_3$+CD$_3$OD) | 0.36 (5:1:1) |
| 24 | 2-F, 4-HO-C$_6$H$_3$ | " | " | 1780,1720,1630, 1518. | — | 0.2 (5:1:1) |
| 25 | 3-Cl, 4-HO-C$_6$H$_3$ | " | " | 1781,1717. | — | 0.27 (5:1:1) |
| 26 | 2-Cl, 4-HO-C$_6$H$_3$ | Tetr | powder | 1781,1717 | — | 0.28 (8:1:1) |
| 27 | 3-CF$_3$, 4-HO-C$_6$H$_3$ | " | " | 3400,1785,1723br. | — | 0.56 (5:1:1) |
| 28 | 3-F, 4-HO-C$_6$H$_3$ | " | " | — | — | 0.19 (8:1:1) |
| 29 | 2-OH, 5-F-C$_6$H$_3$ | " | " | 3360,1780,1720, 1610,1515. | — | 0.38 (8:1:1) |
| 30 | 3-F, 5-Cl, 4-HO-C$_6$H$_2$ | " | " | 1782,1721. | — | 0.39 (8:1:1) |
| 31 | 2,3-Cl$_2$, 4-HO-C$_6$H$_2$ | " | powder (m.p.133°C.) | 3310,1788,1729, 1635. | — | 0.5 (5:1:1) |
| 32 | 3,5-Cl$_2$, 4-HO-C$_6$H$_2$ | " | powder | 1781,1719. | — | 0.33 (8:1:1) |
| 33 | 3-F, 4-HO-C$_6$H$_3$ | Tdz | powder | 1775,1700,1497. | — | 0.5 (5:1:1) |
| 34 | " | MeTdz | " | 1780,1704,1498. | — | 0.46 (5:1:1) |
| 35 | 2-F, 4-HO-C$_6$H$_3$ | Tdz | " | 1780,1720,1630, 1600 | — | 0.58 (5:1:1) |

Table 4-continued

Physical constants of Products (i')

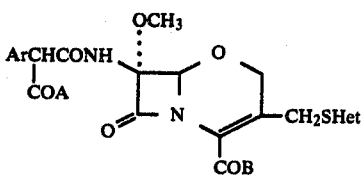

(i')

| Compound (i') | | | IR:$\nu_{max}^{CHCl_3}$ | NMR:$\delta_{ppm}^{CDCl_3}$ | TLC:Rf/SiO$_2$ |
|---|---|---|---|---|---|
| No. | Ar | Het | State | (Hz values show | (EtOAc+HOAc |
| | | | (cm$^{-1}$) | coupling constants) | +H$_2$O) |
| 36 | " | MeTdz | " | 1781,1708,1503. | — | 0.46 (5:5:1) |

What we claim is:

1. A compound of the formula

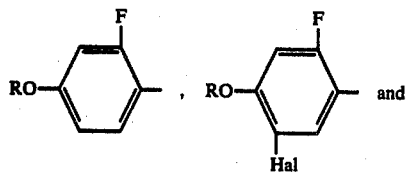

wherein Ar is a member of the group consisting of

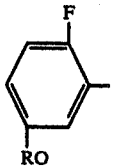

wherein RO is hydroxy or conventionally protected hydroxy, Hal is fluoro or chloro; COA and COB each represents a member of the group consisting of carboxy, conventionally protected carboxy and a pharmaceutically acceptable carboxylic acid carboxy salt group and Het represents 1-methyltetrazol-5-yl.

2. A compound according to claim 1 wherein Ar is 2-fluoro-4-hydroxyphenyl.

3. A compound according to claim 1 wherein the pharmaceutically acceptable carboxylic acid salt group is a sodium, potassium, magnesium or calcium carboxylic acid salt.

4. A compound according to claim 1 wherein the conventionally protected carboxy group is a carboxy group protected by phthalidyl, acetoxymethyl, pivaloyloxymethyl, acetoxyethyl, propionyloxyethyl, indanyl, phenyl, tolyl, dimethylphenyl, methoxyphenyl, methoxycarbonyloxyethyl, ethoxycarbonyloxyethyl, or phenacyl.

5. A compound according to claim 1, said compound being selected from the group consisting of
7β-[α-(2-fluoro-4-hyroxyphenyl)-α-carboxyacetamido]-7α-methoxy-3-(1-methyltetrazol-5-yl)thiomethyl-1-dethia-1-oxa-3-cephem-4-carboxylic acid,
7β-[α-(2-fluoro-4-hydroxyphenyl)-α-carboxyacetamido]-7α-methoxy-3-(1-methyltetrazol-5-yl) thiomethyl -1-dethia-1-oxa-3-cephem-4-carboxylic acid sodium salt,
7β-[α-(2-fluoro-5-hydroxyphenyl)-α-carboxyacetamido]-7α-methoxy-3-(1-methyltetrazol-5-yl) thiomethyl -1-dethia-1-oxa-3-cephem-4-carboxylic acid,
7β-[α-(2-fluoro-5-hydroxyphenyl)-α-carboxyacetamido]-7α-methoxy-3-(1-methyltetrazol-5-yl) thiomethyl -1-dethia-1-oxa-3-cephem-4-carboxylic acid sodium salt,
7β-[60 -(2-fluoro-5-chloro-4-hydroxyphenyl)-α-carboxyacetamido]-7α-methoxy-3-(1-methyltetrazol-5-yl)thiomethyl-1-dethia-1-oxa-3-cephem-4-carboxylic acid,
7β-[α-(2-fluoro-5-chloro-4-hydroxyphenyl)-α-carboxyacetamido]-7α-methoxy-3-(1-methyltetrazol-5-yl)thiomethyl-1-dethia-1-oxa-3-cephem-4-carboxylic acid sodium salt,
7β-[α-(2,5-difluoro-4-hydroxyphenyl)-60 -carboxyacetamido]-7α-methoxy-3-(1-methyltetrazol-5-yl) thiomethyl -1-dethia-1-oxa-3-cephem-4-carboxylic acid, and
7β-[α-(2,5-difluoro-4-hydroxyphenyl)-α-carboxyacetamido]-7α-methoxy-3-(1-methyltetrazol-5-yl) thiomethyl -1-dethia-1-oxa-3-cephem-4-carboxylic acid sodium salt.

6. An antibacterial composition which comprises an antibacterially effective amount of a compound according to claim 1 in admixture with a pharmaceutically acceptable carrier.

7. An antibacterial composition according to claim 6 in the form of a solution for injection.

8. A method for the treatment of a bacterial infection which comprises administering to a human or veterinary subject suffering from said bacterial infection an antibacterially effective amount of a compound according to claim 1.

* * * * *